United States Patent [19]

Barcelo et al.

[11] Patent Number: 4,960,881
[45] Date of Patent: Oct. 2, 1990

[54] ALPHA-CHLORINATED CARBONATES, THEIR METHOD OF MANUFACTURE AND APPLICATION IN THE PROTECTION OF THE AMINE FUNCTIONS OF AMINO ACIDS

[75] Inventors: Gerard, Barcelo, Genevieve Des Bois; Jean-Pierre Senet, Buthiers; Gerard Sennyey, Saint-Aubin, all of France

[73] Assignee: Societe Nationale Des Poudres et Explosifs, Paris Cedex, France

[21] Appl. No.: 203,471

[22] Filed: Jun. 6, 1988

Related U.S. Application Data

[60] Continuation-in-part of Ser. No. 893,651, Aug. 6, 1986, abandoned, which is a division of Ser. No. 701,429, Feb. 14, 1985, Pat. No. 4,652,665.

[30] Foreign Application Priority Data

Feb. 16, 1984 [FR] France .................. 84 02328

[51] Int. Cl.$^5$ .................. C07D 499/48; C07D 207/08
[52] U.S. Cl. ...................... 540/326; 546/14; 546/226; 548/406; 548/528; 548/533; 556/420; 558/392; 558/441; 560/13; 560/16; 560/17; 560/24; 560/29; 560/30; 560/31; 560/32; 560/132; 560/136; 560/148; 560/157
[58] Field of Search .............. 560/160, 29, 13, 16, 560/17, 24, 30, 31, 32, 132, 136, 148, 157, 159, 163; 548/533, 406, 528; 546/14, 226; 558/392, 441; 540/326

[56] References Cited

U.S. PATENT DOCUMENTS

| | | | |
|---|---|---|---|
| 3,467,690 | 9/1969 | Chamberlin | 260/463 |
| 3,875,207 | 4/1975 | Iselin et al. | 260/463 |
| 3,944,590 | 3/1976 | Iselin et al. | 260/463 |
| 4,440,692 | 4/1984 | Kalbacher et al. | 260/403 |

FOREIGN PATENT DOCUMENTS

| | | |
|---|---|---|
| 0040153 | 11/1981 | European Pat. Off. |
| 1549816 | 12/1967 | France |
| 828871 | 2/1960 | United Kingdom |
| 1426717 | 3/1972 | United Kingdom |

OTHER PUBLICATIONS

C.A. 51:7148f (1957), Hales et al.
McOmie, "Protective Groups in Organic Chemistry", (1973), p. 58: Plenum Press, London & N.Y.
Fieser et al., "Reagents for Org. Syn." (1967), vol. 1, pp. 97-98.
Fieser et al., "Reagents for Org. Syn." (1969), vol. 2, pp. 54 or 56.
Fieser et al., "Reagents for Org. Syn". (1974), vol. 4, p. 128.
Fieser et al., "Reagents for Org. Syn", (1975), vol. 5, p. 86.
Fieser et al., "Reagents for Org. Syn", (1979), vol. 7, p. 91.
Anderson et al.—t-Butyloxycarbonylamino Acids and Their Use in Peptide Synthesis—Journal Amer. Chem. Soc. pp. 6180-6183 (1957), vol. 79.
Broadbent et al.—Polypeptides, Part V.$^1$. The Use of t-Butyl 2,4,5-Trichlorophenyl Carbonate in the Synthesis of N-t-Butoxycarbonyl Amino-Acids and their 2,4,5-Trichlorophenyl Esters J. Chem. Soc. (C) (1967), pp. 2632-2636.
Mahmoud Jaouadi—THESE Dec. 14, 1984, pp. 56,55.
Barry M. Pope et al.—Organic Syntheses, vol. 57 (1977), pp. 45-49.

Primary Examiner—Joseph Paul Brust
Attorney, Agent, or Firm—Bucknam and Archer

[57] ABSTRACT

The invention relates to carbonates of formula:

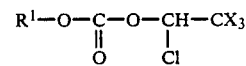

in which X is a fluorine, chlorine or bromine atom and R$^1$ is different from the

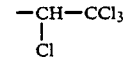

group and represents: a substituted or non-substituted, saturated or unsaturated, aliphatic, araliphatic, primary, secondary, tertiary or cycloaliphatic radical. These α-chlorinated carbonates are prepared by the action of a compound of formula R$^1$OH on a chloroformate of formula:

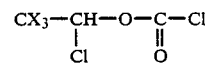

in a solvent medium in the presence of an acid scavenger which is added after the two preceding compounds. They are used to block the amine function of amino acids. The α-chlorinated carbonate and amino acid are reacted in a solvent medium at a temperature of −5° to 100° C. in the presence of an acid scavenger. Blocked amines are very useful in peptide synthesis.

18 Claims, No Drawings

ALPHA-CHLORINATED CARBONATES, THEIR METHOD OF MANUFACTURE AND APPLICATION IN THE PROTECTION OF THE AMINE FUNCTIONS OF AMINO ACIDS

This application is a continuation-in-part of U.S. Ser. No. 893,651, filed Aug. 6, 1986 which was a divisional of U.S. Ser. No. 701,429, filed Feb. 14, 1985. The latter has now issued as USP 4,652,665 on Mar. 24, 1987 Ser. No. 893,651 has now been abandoned.

The invention relates to new α-chlorinated carbonates, their method of manufacture and application in the protection of the amine functions of amino acids.

Carbonates are compounds in treat demand because they are used in a large variety of fields such as solvents, plasticisers, lubricants, transesterification agents or intermediates in the production of peptides.

To perform syntheses in which amino acids are involved, the amine function of these acids must be protected temporarily. This amine function is very often blocked by conversion into a carbamate function which presents racemisation when coupling and is readily cleaved, for example, by acidolysis, hydrogenolysis, or any other known method (E. Schroeder and K. Lubke, "The Peptides", Vol. 1, page 39, Academic Press, New York and London, 1965).

The most commonly used groups for that purpose are:
benzyloxycarbonyl carbonate (Z),
tert-butyloxycarbonyl (BOC),
fluorenylmethyloxy carbonyl (FMOC),
trichloroethyloxycarbonyl (TROC),
vinyloxycarbonyl (VOC).

The tertiary butyloxycarbonyl (BOC) group is particularly in demand.

These protecting groups are generally introduced by the action of the corresponding chloroformate on the amine function.

However, chloroformates cannot always be used. Some are not very stable or else they are difficult to manipulate. This is the case, for example, of p-methoxybenzyl, furfuryl or tertiary-butyl chloroformates. The last of these, for example, even when prepared in situ is not satisfactory because of the formation of urea in the presence of excess phosgene.

Other carbamation agents have been suggested such as:

azides of various protecting groups. Their synthesis is achieved in several stages and is difficult. They can decompose explosively, like the azide of BOC;

fluorides of BOC, p-methoxybenzyl or furfuryl, but their preparation is difficult because this requires the use of commercially not available raw materials such as ClCOF or BrCOF, which must be manipulated with caution.

Some experiments have been carried out with some particular carbonates, such as the mixed carbonates of protecting groups and phenyl, which may be unsubstituted or substituted. These methods, however, present many drawbacks. The carbonates being used are difficult to prepare and do not react with all amino acids. A phenol is formed which is difficult to remove and the reaction is reversible, a fact which leads to low yields.

As stated by Anderson et al , J. Chem. Soc. 79, 6180–6183 (1957) the tert-butyl phenyl carbonate is difficult to prepare (see page 6180, right column, lines 8–9 from the bottom). French patent 1,549,816 reports that tert-butyl p-nitrophenyl carbonate does not react with certain amino acids.

Anderson did not report any experiment with threonine, glutamic acid and aspartic acid. The results reported by Anderson are very unsatisfactory with isoleucine and valine. With l-alanine and proline, Anderson reported low yields.

The removal of phenol and p-nitrophenyl formed as by-products presents difficulties, because the solubility of the protected amine and phenol or p-nitrophenol is close, both in organic as well as aqueous solvents. Therefore several operations of washing, extraction and filtration are required.

Broadbent, J. Chem. Soc. (1967) 2632 proposed the use of 2,4,5-trichlorophenyl tert-butyl carbonate but the separation of the trichlorophenol by-product requires several steps of solubilization, acidification and extraction. Further this reference stated that in the case of hydroxyamino acids such as serine and threonine the reaction fails and in the case of tyrosine the yield is only 38%. Further, this reaction requires a warming at 45°–65° C.

Dicarbonates of protecting groups have been proposed, such as di-tert-butyl carbonate but the synthesis of these compounds is expensive and difficult. Organic Syntheses (1977) 57, pp 45–50 shows the difficulties in the preparation of di-t-butyl carbonate, three steps and obviously a long preparation. The overall yield is only 50%. In any event this reagent is expensive because one-half of the reagent is lost. The removal of tert-butyl alcohol by-product presents the same difficulties as the phenols mentioned hereinabove.

Carbonates of oxime, hydroxysuccinimide, enol or 5-dimethyl-pyrimidyl have also been proposed but they are also difficult to prepare and require costly raw materials.

The foregoing demonstrates that there has been a need in the art for some new compounds which are easy to make with good yields and are stable, which can be used without difficulty to attach the most important protecting groups onto the amine function of amino acids and which do not have the disadvantages of the previously mentioned compounds.

According to the invention the new α-chlorinated carbonates have the general formula:

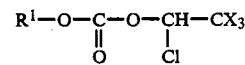

in which X is a fluorine, chlorine or bromine atom and $R^1$ is different from

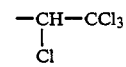

and represents: a substituted or non-substituted, saturated or unsaturated, aliphatic, araliphatic, primary, secondary, tertiary or cycloaliphatic radical.

In preference, X is a chlorine atom and $R^1$ a saturated or ethylenically unsaturated, substituted or non-substituted primary, secondary or tertiary $C_1$ to $C_{20}$ alkyl or $C_7$ to $C_{20}$ aralkyl radical. The substituents of $R^1$ can be very varied. They are, for example, halogen atoms, $C_1$ to $C_6$ trialkylsilyl or nitro groups.

In particular, $R^1$ is chosen from groups normally used to protect the amine functions in the form of carbamates, such as tertiary butyl, paranitrobenzyl, 9-fluorenylmethyl, 2,2,2-trichloroethyl, trimethylsilylethyl.

According to the invention, the new α-chlorinated carbonates are prepared by reacting the hydroxylated compound of formula $R^1OH$ with an α-chlorinated chloroformate of formula:

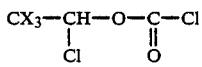

X and $R^1$ having the same meaning as before, in a solvent medium at a temperature of −20° to +50° C. in the presence of a hydrochloric acid scavenger which is added after the two reagents.

The following reaction takes place:

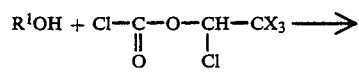

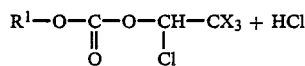

The solvent medium consists of one or several solvents inert to the reagents. Chlorinated aliphatic solvents, for example, dichloromethane or dichloroethane, cyclic or acyclic ethers, ketones, such as acetone or 2-butanone, nitriles, esters or aliphatic or aromatic hydrocarbons are chosen preferentially.

The acid scavenger is generally an organic base or inorganic base. Pyridine or triethylamine are used preferentially.

The base is added after the two reagent compounds, preferably gradually.

The temperature is preferentially between −5° and +5° C. On completion of the reaction the temperature of the mixture can be raised to the ambient temperature for a few minutes to several hours.

The α-chlorinated chloroformates themselves can be prepared by chlorination of chloroformates or preferably by phosgenation of the corresponding aldehydes as described in European Patent No. 40153.

The starting compounds and the base are generally introduced in stoichiometric quantity. An excess of alcohol can be used. The carbonate obtained is easily isolated by the usual methods.

The carbonates of the invention have never until now been described in the literature. The presence of a

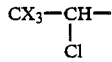

group in their structure gives them very specific properties which make them very useful as intermediates in synthesis.

The invention relates in particular to an application of the new α-chlorinated carbonates.

In this application, the previously described α-chlorinated carbonates are used to protect the amine function of amino acids.

Within the scope of the present invention, the term "amino acid" means an organic compound containing at least one carboxyl group and at least one unsubstituted or substituted amino group or an imino group, still containing at least one hydrogen atom, of molecular weight up to 1000, of general formula

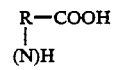

The reaction proceeds as follows:

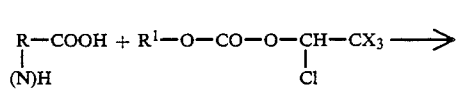

More specifically the amino acids are reacted in a solvent medium in the presence of a hydrochloric acid scavenger at a temperature between −5° and 100° C. with an amino and/or imino carboxylic acid including at least one hydrogen atom on the amino or imino group. Specifically the amino and/or imino carboxylic acid are represented by the formula

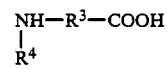

in which $R^3$ and $R^4$ are as defined hereinbelow.

The radical $R^4$ is a hydrogen atom or lower alkyl of 1–4 carbon atoms and $R^3$ is a linear or branched, substituted or unsubstituted, saturated $C_1$ to $C_{20}$ alkylene, or $C_2$–$C_{20}$ linear or branched alkenylene or $C_3$–$C_6$ cycloalkylene radical. The $C_1$–$C_{20}$ alkylene, $C_2$–$C_{20}$ alkenylene and cycloalkylene radicals may be unsubstituted or substituted by a substituent which is —COOH, —NH$_2$, —CONH$_2$, —NH, mercapto, hydroxyl, 1 α carbon atoms alkylthio, 5-imidazolyl, β-indolyl, guanidino, phenyl or phenoxyphenyl. The phenyl group may be substituted by halogen or hydroxyl or both halogen and hydroxyl.

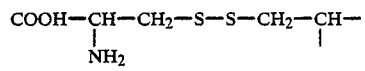

or may be 6-aminopenicillanic acid of formula

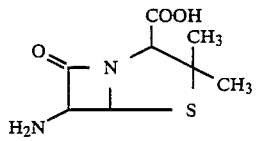

It is also possible that $R^3$ and $R^4$ form with the N atom to which they are bound the radical of proline or hydroxyproline.

The reaction can be represented by the equation hereinbelow:

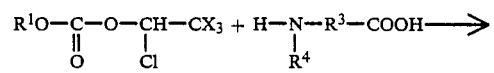

-continued

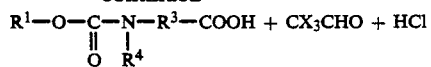

This reaction is surprising as there is an elimination of HCl but not with attachment of the amino group to the carbon atom to which the chlorine is attached such as:

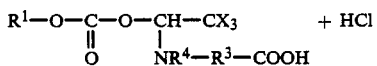

as would normally be expected and as is the case for example when an α-chlorinated compound reacts with an acid:

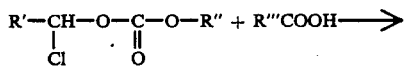

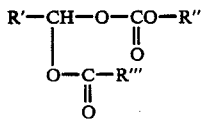

as described in ASTRA - French Patent No. 2 201 870, which corresponds to British 1,426,717.

On the contrary the new α-chlorinated compounds cleave, the radical,

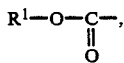

attaches itself to the nitrogen atom of the amino acid and an aldehyde, $CX_3CHO$, is formed.

As starting amino acids or imino carboxylic acids can be used natural or synthetic, optically active or inactive, or racemic amino or imino carboxylic acids still containing one hydrogen atom fixed onto the amino or imino group. The reaction is independent of the nature of $R^3$ and $R^4$ and the only requirement is that one hydrogen atom be attached to the N atom.

For instance, the reaction is applicable to glycine, alanine, valine, leucine, isoleucine, phenlalanine, serine, threonine, lysine, δ-hydroxylysine, arginine, aspartine acid, asparatine, glutamic acid, sarcosine, glutamine, cysteine, cystine, methionine, tyrosine, phenylglycine, thyroxine, proline, hydroxyproline, tryptophan, histidine, niroarginine, also non-protein amino acids. The reaction is also applicable to allo-isoleucine, allo-threonine, alpha-amino, adipic acic, alpha-amino butyric acid, 7-amino heptanoic acid, gamma-amino butyric acid, epsilon-amino caproic acid, 3,4-dehydroproline, dehydroalanine, 3,5-dibromo tyrosine, 3,5-diiodo tyrosine, p-fluoro phenyl-alanine, p-iodo phenyl-alanine, p-bromo phenyl-alanine, homoproline, isoglutamine, isoserine, 1-amino cyco-hexanoic acid, 6-amino penicillanic acid, thyronine, norleucine norvaline, ornithine, statine, beta-alanine, gamma-methyl glutamic acid, gamma-tert-butyl glutamic acid, gammabenzyl glutamic acid and 1-aminocyclopropanoic acid.

The reaction is also applicable to amino acids in which the imino group is part of a 4-member ring, such as azetidine 2-carboxylic acid.

The functional groups which may be present in the amino acids, attached to the group $R^3$ may be protected with one of the radical conventionally used in amino acid chemistry, as described in Houben Weyl, Vol. 15, "Syntheses von Peptiden"(1974) pp. 1-2 7. For instance, the benzyloxycarbonyl, tosyl, benzyl, acetamido- methyl, tert-butyloxy carbonyl, 9-fluorenylmethyloxy-carbonyl, tert-butyl, trichloroethyloxy-carbonyl, vinyloxycarbonyl, $NO_2$.

For instance:

The benzyloxycarbonyl group may be used to protect an $-NH_2$ group;

The benzyl group may be used to protect a —COOH group;

The tosyl group may be used to protect an —NH group (in an imidazolyl ring or in arginine);

The acetamidomethyl group may be used to protect an SH group;

The t-butyloxycarbonyl group may be used to protect an $NH_2$ group;

The 9-fluorenymethoxycarbonyl group may be used to protect an NH2 group;

The t-butyl group may be used to protect a —COOH or an OH group;

The trichloroethyloxycarbonyl group may be used to protect an $NH_2$ group

The vinyloxycarbonyl group may be used to protect an $-NH_2$ group;

The $NO_2$ group may be used to protect an $-NH_2$ group.

The amino acid can be in the form of one of its derivatives, for example, an ester or an amide, or other substitution products and amides referred to in the Houben Weyl book cited hereinabove, such as ethylglycinate, $N^{im}$-tosyl histidine, gamma benzyl glutamic acid, O-benzyl tyrosine, O-benzyl serine, O-benzyl threonine, epsilon benzyloxycarbonyl lysine, S-acetamidomethyl cysteine, tert-butyl glycine, beta-cyano-alanine, neopentyl-glycine, p-hydroxy-phenyl-glycine, delta-N-benzyloxycarbonyl ornithine, O-methyl serine, O-tert-butyl serine, O-methyl threonine, O-tert-butyl threonine, O-acetyl tyrosine, O-methyl tyrosine, O-2-bromobenzyloxycarbonyl tyrosine, O-2-chlorobenzyloxycarbonyl tyrosine, O-tert-butyl tyrosine, alanine methyl ester, N-methyl alanine, alpha-methyl alanine, $N^G$ - (4-methoxy-2,3,6-trimethylbenzenesulfonyl) arginine, $N^G$ -tosyl arginine, $N^G$ -mesitylenesulfonyl arginine, beta-benzyl ester of aspartic acid, beta-tert-butyl ester of aspartic acid, beta-methyl ester of aspartic acid, gamma-carboxy-glutamic acid, gamma, gamma' -di tert butyl ester of glutamic acid, S-benzyl cysteine, S-diphenylmethyl cysteine, S-methoxybenzyl cysteine, S- (4-methylbenzyl) cyseine, S-trityl cysteine, S-tert-butyl cysteine, $N^{im}$. benzyl histidine, $N^{im}$ -mesitylenesulfonyl histidine, O-tert-butyl hydroxyproline, epsilon-acetyl lysine, epsilon BOC lysine, epsilon-trifluoroacetyl lysine, epsilon-2-bromobenzyloxycarbonyl lysine, epsilon-2-chlorobenzyloxycarbonyl lysine. The aminoacid is in the D, L or d,l form.

The invention usually applies to alpha amino acids but beta, gamma and delta amino acids can also be used.

The carboxylic group can also be replaced by a sulfonic or phosphoric group.

As α-chlorinated carbonates are used preferentially those in which X is a chlorine atom and the radical $R^1$ one of the most commonly used protecting groups to acylate the amine function, for example, 1,2,2,2 tetrachloro-ethyl and 2', 2', 2' trichloroethyl carbonate, 9-fluorenylmethyl and 1,2,2,2-tetrochloroethyl carbonate, paranitrobenzyl and 1,2,2,2-tetrachloroethyl carbonate or 2-trimethylsilylethyl and 1,2,2,2-tetrachloroethyl carbnate. THese carbonates are in particular greatly favored in the case of unprotected hydroxyamino acids, such as serine or tyrosine. The 1,2,2,2 tetrachloroethyl and tertiary butyl carbonate and the 1,2,2,2-tetrachloroethyl and 9-fluorenylmethyl carbonate are particularly valuable.

The presence of an acid scavenger is necessary to eliminate the hydrochloric acid which is formed during the reaction. This can be effected by means or an organic or inorganic base.

Among the preferred bases are sodium or potassium hydroxide, sodium or potassium carbonate or bicarbonate, or magnesium oxide, which are generally used in the form of an aqueous solution, or tertiary amines, for example, pyridine and triethylamine.

The basic substance is usually added in excess, preferably about 1 1 to 3 equivalents per amine function to be protected.

It can be advantageous to maintain the pH constant throughout the reaction by means of standard apparatus.

The solvent medium can consist of one or several solvents that are inert to the reagents As preferred organic solvent are chosen preferentially chlorinated aliphatic solvents such as dichloromethane, 1,2 dichloroethane, cyclic or acyclic ethers, for example, tetrahydrofuran or dioxan, acetone, pyridine, acetonitrile, dimethylformamide, alcohols such as ethanol or tertiary butanol. Water can also be used alone or mixed with the above solvents. A 1:1 dioxan/water mixture is particularly favoured.

The reaction temperature depends on the nature of the solvent, the reactivity of the starting compounds, as well as the other reaction conditions. It is preferentially between 0° C. and 30° C.

Atmospheric pressure is the most commonly used pressure. The reaction time is variable. It is generally between 0.5 and 36 hours, usually between 2 and 6 hours.

The starting compounds can be added in stoichiometric quantity. The use of one of the reagents in excess is preferred.

The order in which the reagents are introduced is not a fundamental characteristic of the invention. Generally the α-chlorinated carbonate is added after the amino acid.

The blocked amino acids can be recovered easily and isolated in crystallized form if necessary by converting them into an ammonium salt, for example, a dicyclohexylammonium salt.

Using the new o-chlorinated carbonates of the invention obtained from available raw materials and a simple method according to this invention, the amino function of very varied amino acids can be blocked in the form of carbamates by means of all the known protecting groups. This was impossible or very difficult to achieve until now The yields are very high. The reaction conditions are mild and no racemization occurs.

With the amino acids protected in this way any desired coupling operations with the acid function, as in conventional peptide synthesis, can be carried out (cf. for example, E. Gross and J. Meinhofer Ed. "The Peptides: Analysis - Synthesis Biology", Academic Press, New York and London, Vol. 3, 1980).

These amino acid derivatives are very much used as intermediates in the manufacture of food and pharmaceutical products. The synthesis of ASPARTAM can be cited as an example (cf. tetrahedron, vol. 39, No. 24, pp. 4121 to 4126, 1983, B. YDE, et al.

The invention is illustrated by the following examples.

EXAMPLE 1

Synthesis of 1,2,2,2 tetrachloroethyl and tertiary-butyl carbonate 9.9 (0.04 mole) of 1, 2, 2, 2 tetrachloroethyl chloroformate are added at one time to a solution of tertiary butanol (3 g; 0.04 mole) in dichloromethane (50 ml). After cooling to 0° C., 3.2 g (0.04 mole) of pyridine are added drop by drop. The mixture is stirred for four hours at ambient temperatures. 20 ml of chilled water are then added, the organic phase is separated and washed with 20 ml of chilled water, followed by drying over magnesium sulfate and evaporating the solvent. 11.3 g of a white solid (yield: 99%) are obtained. This is recrystallized from petroleum-ether (yield 87%; m.p.: 70° C.) and 9.9 g of pure carbonate obtained. b.p.: 96° C. /866 Pa (6.5 mm Hg) IR $\nu$CO=1770 cm$^{-1}$ NMR H$^1$(CDCl$_3$, TMS): 1.5 (s, CH$_3$) 6,7 (s, CH)

EXAMPLE 2 a. Preparation of tertiary-butyloxycarbonyl-L-phenylalanine

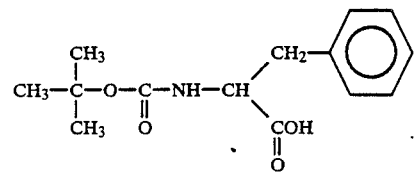

To a solution of L-phenylalanine (1.65 g; 10 mmoles) in aqueous dioxan (1: 1; 30 ml) are added 4.2 ml (30 mmoles) of triethylamine and the mixture stirred until dissolution is complete (about 10min). 2.85 g (10 mmoles) of tertiary butyl and 1, 2, 2, 2 tetrachloroethyl carbonate are then added and the mixture stirred for six hours at 20° C. 50 ml of water are then added and extracted with 2×2 ml of ethyl acetate. The aqueous phase is acidified (pH 2-3) with N HCl and then extracted with 3×30 ml of ethyl acetate. The extract is washed with a saturated NaCl solution, dried over MgSO$_4$ and evaporated. The product obtained is crystallized from ethyl acetate and petroleum-ether. 2.1 g of the desired carbamate are obtained (yield 79%).

85°–87° C.; m.p.$_{Lit}$=86°–88° C., optical rotation $\alpha_D^{20} = +28$ (c 1.5 EtOH; $\alpha_D$ $_{Lit}^{20} = +24.7$ (c 1.5 EtOH).

b. Preparation of N-tertiarybutyloxycarbonyl-L-alanine

The procedure followed is the same as that in Example 2a.

From 1.78 g (20 mmoles) of alanine are obtained 3.4 g of BOC-L-alanine (yield: 90%).

m.p. =80°–81° C.; m.p.$_{Lit}$=83°–84° C. $\alpha_D^{20} = -24.9$ (c 2.1 AcOH); $\alpha_D^{20} = -22.4$ (c 2.1 AcOH)

EXAMPLE 3

Preparation of of tertiary-butyloxycarbonyl-L-proline

The procedure followed is the same as that in Example 2. From 1.15 g (10 mmoles) of L-proline are obtained 1.95 g of the desired carbamate (yield 91%).

m.p.=130°-131° C.; m.p.$_{Lit}$=132°-133° C.

$a_D^{20}$= −60(c 2.0 AcOH); $a_{DLit}^{20}$= −60.2 (c 2.0 AcOH).

EXAMPLE 4

Preparation of tertiary-butyloxycarbonyl-glycine BOC-Gly)

The procedure followed is the same as that in Example 2. From 0.75 g (10 mmoles) of glycine are obtained 1 5 g of the desired carbamate (yield 86%).

m.p.=80°-85° C.; m.p.$_{Lit}$=86°-88° C.

EXAMPLE 5

Preparation of BOC-Gly at controlled pH 5.6 g (0.075 mole) of glycine are dissolved in 150 ml of aqueous dioxan (50%) and the pH adjusted with 4 N caustic soda. 23.6 g (0.083 mole) of 1, 2, 2, 2 tetrachloroethyl and tertiary butyl carbonate are added at one time and the pH maintained constant by addition of 4 N caustic soda. When the reaction is over about 200 ml of water are added and the aqueous phase then washed two times with 100 ml of ethyl-ether. The aqueous phase is then acidified to a pH of 3 with 6 N HCl and extracted three times with 200 ml ethyl acetate (AcOEt). After drying and evaporation of solvent, the product is crystallized from Ac-OEt/O petroleum-ether (40°-70° C.). BOC-glycine which melts at 85°-87° is obtained.

| pH | Time | Caustic soda added | Yield isolated |
|---|---|---|---|
| 10 | 5 h | 2 eq | 45% |
| 9 | 20 h | 2 eq | 71.4% |
| 8 | 30 h | 1 eq | 31% | b. The procedure followed is the same as that in (a) using various amino acids.

The results ar given in the following table:

| Amino acid | pH | Yield % | m.p. °C. | $[\alpha]_D^{20}$ | c/solvent |
|---|---|---|---|---|---|
| Pro | 8.6 | 80 | 135-136 | −60 | 2/AcOH |
| Trp | 8.3 | 74 | 135-140 | −21.2 | 1/AcOH |
| Asp (OBzl) | * | 42 | 98-100 | −19 | 2/DMF |
| His (Tos) | 10 | 50 | 154 | +25.4 | 1/MeOH |
| Ala | 10.1 | 70 | 84 | −25.5 | 2/AcOH |
| Val | 9.5 | 80 | 78 | −6.0 | 1/AcOH |
| Ile | 9.5 | 71 | 66 | +3.3 | 1/AcOH |
| Leu | 9.75 | 95 | 75 | −27 | 1/AcOH |
| Met | 9.7 | 75 | oil | — | — |
| Glu (OBzl) | 9 | 42 | 132 (DCHA salt) | +13.6 | 1.1/MeOH |
| His (Tos) | * | 50 | 154 | +25.4 | 1/MeOH |
| Tyr (Bzl) | 9.8 | 43 | 98-100 | +27.4 | 2/EtOH |
| Ser (Bzl) | 9.5 | 74 | 61 | +21 | 2/EtOH 80% |
| Thr (Bzl) | 9.0 | 76 | 114 | +16.3 | 1/MeOH |
| Arg (NO$_2$) | 9.5 | 25 | 100-114 | −23.0 | 1.9/pyridine |
| Cys (Acm) | 9.5 | 46 | — | — | — |
| Lys (Z) | 10.2 | 84 | oil | — | — |

* based used: triethylamine

EXAMPLE 6

Preparation of tertiary-butyloxycarbonyl-L-tyrosine 1.81 g (10 mmoles) of tyrosine are dissolved in 20 ml of aqueous dioxan (1: 1) by adding 1.4 ml (10 mmoles) of triethylamine and 15 mmoles of caustic soda. 2.85 g (10 mmoles) of tertiary butyl and 1, 2, 2, 2 tetrachloroethyl carbonate are then added and the mixture stirred for six hours at 20 ° C. The procedure followed is the same as that in Example 2. The product obtained is crystallized as the dicyclohexyl ammonium salt. 3.8 g are obtained (yield 82%).

m.p. =206° C.; m.p.$_{Lit}$=212° C.

EXAMPLE 7

Preparation of tertiary-butyloxycarbonyl-L-serine

The procedure followed is the same as that in Example 2, but the reaction time is 24 hours instead of 6 hours. From 1.05 g (10 mmoles) of L-serine are obtained 3.1 g of the desired carbamate as the dicyclohexyl ammonium salt (yield 78%).

m.p.=139°-140° C.; m.p.$_{Lit}$=140°-142° C.

$a_D^{20}$=+8 (C 2.8 MeOH); $a_D$ $_{Lit}^{20}$=+13 (c=MeOH).

EXAMPLE 8

Preparation of tertiary-butyloxycarbonyl-L-aspartic acid

The procedure followed is the same as that in the preceding example.

From 1.33 g (10 mmoles) of L-aspartic acid, 1.4 g of the desired acid is obtained (yield 60%.

m.p.=116°-118° C.; m.p.$_{Lit}$=114°-116° C.

$a_D^{20}$= −5 (c 1.0 MeOH); $a_D$ $_{Lit}^{20}$= −6.2 (c 1.0 MeOH).

EXAMPLE 9

Preparation of 1, 2, 2, 2 tetrachloroethyl and 9-fluorenylmethyl carbonate

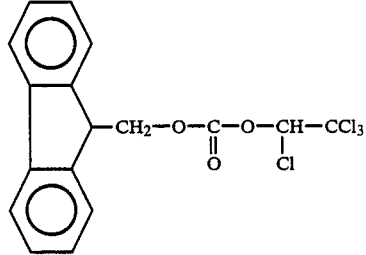

6.7 (0.027 mole) of 1, 2, 2, 2 tetrachloroethyl chloroformate are added at one time to a solution of 9-fluorenylmethanol (4.9 g; 0.025 mole) in 50 ml dichloromethane. The mixture is cooled to 0° C. and 2.2 ml of pyridine are added drop by drop. The mixture is stirred for four hours at 0° C. 50 ml of dichloromethane are then added and the organic phase washed twice with 50 ml of chilled water. Drying takes place over magnesium sulfate and the solvent is evaporated. The residue is crystallized from hexane and 9.3 g of the desired carbonate obtained (yield 98%).

m.p.=98°-100° C.

IR: $\nu$C=0 1750 cm$^{-1}$

NMR H$^1$: (CDCl$_3$, TMS) 4.5 ppm CH$_2$—0; 6.75 ppm

EXAMPLE 10

Preparation of 9fluorenylmethyloxycarbonyl-L-phenylalanine

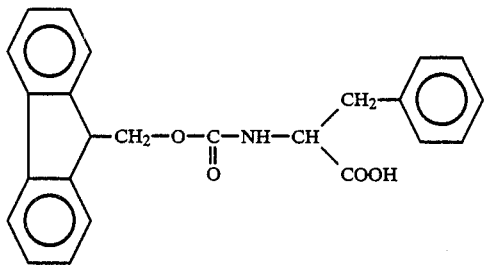

0.83 g of L-phenylalanine (5 mmoles) are dissolved in aqueous dioxan (1: 2, 12 ml) containing 1.4 ml of triethylamine (10 mmoles). The mixture is cooled to 0° C. and 2.05 g (5 mmoles of the preceding carbonate dissolved in 4 ml of dioxan added at one time. After two hours at 0° C., 20 ml of water are added, followed by extraction twice with 20 ml of ether. The aqueous phase is then acidified (pH 2-3) with 6 N HCl followed by extraction three times with 50 ml of ethyl acetate. This is followed by drying over $MgSO_4$ and evaporation. The product obtained crystallizes from ethyl acetate and petroleum-ether, and 1.44 g of the desired derivative obtained (yield 75%).

m.p.=178°-179° C.

m.p.$_{Lit}$=178°-179° C. (Lit: L Lapasantis et al., Synthesis (1983) 671).

EXAMPLE 11

Preparation of 9-fluorenylmethyloxycarbonyl (L)-Proline (FMOC-Pro)

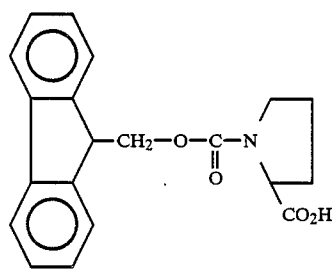

The procedure followed is the same as that in Example 10. From 0.58 g (5 mmoles) of L-Proline are obtained 1.4 g of FMOC-L-Proline (yield 83%).

m.p.=112°-113° C.; m.p.$_{Lit}$=116°-117° C.

EXAMPLE 12

Preparation of 9-fluorenylmethyloxycarbonyl-L-serine

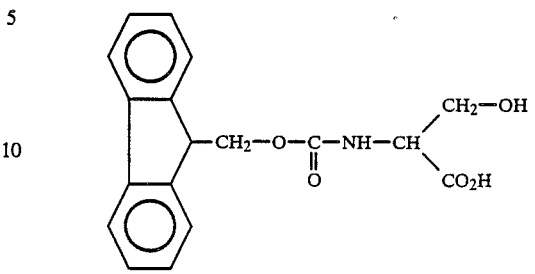

The procedure followed is the same as that in Example 10, but the reaction is continued for 24 h at 20° C. From 0.53 g (5 mmoles) of L-serine are obtained 1.32 g of FMOC-(L)-serine (yield 81%).

m.p.=73°-75° C.

After recrystallization the m.p.=83°-86° C.; m.p.$_{Lit}$=86°-88° C.

EXAMPLE 13

Preparation of 2, 2, 2 trichloroethyl and 1', 2', 2', 2' tetrachloroethyl carbonate

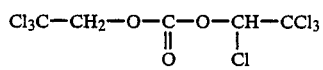

The procedure followed is the same as that in Example 1. From 14.9 g of trichloroethanol (0.1 mole) are obtained 24.1 g of the desired carbonate (yield 67%).

b.p.=108°C./6.6 Pa; m.p.=36° C.

IR $\nu CO=1770$ cm$^{-1}$

NMR H$^1$ (CDCl$_3$, TMS): 4.85 (s, CH$_2$) 6.7 (s, CH).

EXAMPLE 14

Preparation of trichloroethoxycarbonyl-L-phenylalanine-TROC-L-Phe)

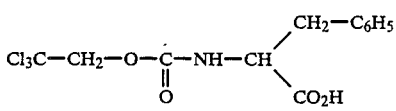

The procedure followed is the same as that in Example 10. From 0.83 g (5.5 mmoles) of L-phenylalanine and 1.98 g (5.5 mmoles) of 2, 2, 2 trichloroethyl and 1', 2', 2', 2'tetrachloroethyl carbonate are obtained 1.43 g of TROC-L-phenylalanine (yield 84%).

m.p.=128°-129° C.; m.p.$_{Lit}$=129°-130° C.

EXAMPLE 15

Preparation of trichloroethyloxycarbonyl-(L)-serine

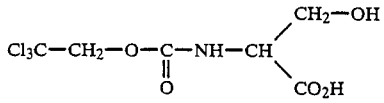

The procedure followed is the same as that in Example 12. From 0.53 g (5 mmoles) of L-serine and 1.98 g (5.5 mmoles) of carbonate of EXAMPLE 13 are obtained 1.15 g of TROC-L-Serine (yield 82%).

m.p.=111°-113° C.; m.p.$_{Lit}$=114°-115° C.

EXAMPLE 16

Preparation of 1, 2, 2, 2 tetrachloroethyl and 2-trimethylsilylethyl carbonate

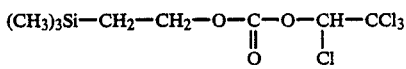

The procedure followed is the same as that in Example 1. From 5.91 g of trimethylsilylethyl and 12.35 g of tetrachloroethyl choroformate are obtained 13.6 g of the desired product (yield 83%).

b.p.=92°-94° C./6.6 Pa.
IR $\nu CO = 1750$ 1 cm$^-$
NMR H$^1$ (CDCl$_3$, TMS external)=0.1 (s, CH$_3$—Si) 1.1 (t, CH$_2$—Si) 4.35 (t, CH$_2$—0) 6.7 (s, CH—Cl)

EXAMPLE 17

Preparation of trimethylsilylethyloxycarbonyl-(L)-phenylalanine

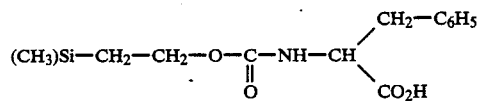

The procedure followed is the same as that in Example 12 From 0 83 g (5 mmoles) of phenylalanine and 1.8 g (5.5 mmoles) of the preceding carbonate are obtained 1 4 g of trimethylsilylethoxycarbonyl-L-phenylalanine as an oil (yield 100%).

NMR H$^1$ (CDCl$_3$, TMS) 0 (s, CH$_3$—Si) 0.9 (t, CH$_2$—Si) 3.0 (CH$_2$Ph) 4.0 (t, 0-CH$_2$—C—Si) 4.5

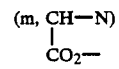

5.2 (s, NH) 7.2 (s, Ph —H) 8.7

2 ml of dicyclohexylamine are added to this oil dissolved in 5 ml of ether and after crystallization 1.93 g of the dicyclohexylammonium salt obtained (yield 78%).
m.p.=111°-112° C.

EXAMPLE 18

Synthesis of p-nitrobenzyl and 1,2,2,2-tetrachloroethyl carbonate 3.83 g (25 mmoles) of p-nitrobenzyl alcohol and 6.17 g (25 mmoles) of 1,2,2,2-tetrachloroethyl chloroformate are dissolved in 50 ml of dichloromethane. After cooling to 0° C., 2.02 ml of pyridine are added drop by drop. The mixture is stirred for four hours at 10° C. and 50 ml of chilled water then added. The organic phase is separated, followed by further washing twice with 50 ml of water. The organic phase is dried over magnesium sulfate and the solvent evaporated. 8.7 g of the desired product are obtained (yield 96%).

b.p.=190°-195° C./0.05 mm Hg.
m.p.=53°-55° C. (Crystallization solvent: aqueous ethanol; crystallization yield: 54%).

What is claimed is:

1. A method of blocking the amino or imino group of a compound which is an amino or imino carboxylic acid of molecular weight up to 1,000 which is
   (a) R$^4$—NH —R$^3$—COOH wherein R$^4$ is hydrogen or lower alkyl of 1-4 carbon atoms and R$^3$
   (1) is linear or branched C$_1$-C$_{20}$ alkylene or C$_2$-C$_{20}$ linear or branched alkenylene or C$_3$-C$_6$ cycloalkylene radical which are unsubstituted or substituted with at least one substituent which is carboxyl or ester thereof, amino, NH, =NH, substituted amino, substituted =NH, —CONH$_2$, benzyl, cyano, mercapto, substituted mercapto, hydroxy, substituted hydroxy, 5-imidazolyl, substituted imidazolyl, 3-indolyl, guanidino, substituted guanidino, phenyl or phenoxyphenyl, said phenyl or phenoxyphenyl being unsubstituted or substituted by (1) halogen, (2) hydroxy, (3) both halogen and hydroxy, or (4) substituted hydroxy;
   (2) or R$_3$ is

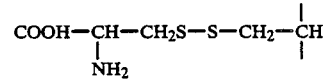

or (b) the compound is proline, 3,4-dehydro-proline, homoproline, hydroxyproline, said hydroxyproline being unsubstituted or substituted, or azetidine;

or (c) the compound is 6-aminopenicillanic acid which consists of reacting said compound with an alpha-chlorinated carbonate of formula:

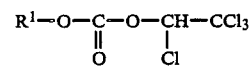

wherein R$^1$ is different from

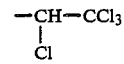

and is a saturated or ethylenically unsaturated primary, secondary or tertiary C$_1$-C$_{20}$ alkyl or C$_7$-C$_{20}$ aralkyl, said R$^1$ being unsubstituted or substituted with at least one substituent which is a member selected from the group consisting of halogen, C$_1$-C$_6$ trialkylsilyl and nitro, in a solvent medium in the presence of an acid scavenger at a temperature between −5° C. and 100° C., whereby the amino or imino group of said amino or imino carboxylic acid is blocked by the group

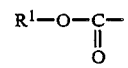

and isolating said blocked amino or imino carboxylic acid from the reaction mixture.

2. The method according to claim 1 wherein the solvent is at least a member selected from the group consisting of dichloromethane, dichloroethane, cyclic ethers, acetone, pyridine, acetonitrile, dimethylformamide, alcohols and water.

3. The method according to claim 2 wherein the solvent contains water.

4. The method according to claim 3 wherein the solvent is a dioxane-water mixture in a ratio of 1:1.

5. The method according to claim 1 wherein the acid scavenger is an organic or inorganic base.

6. The method according to claim 5 wherein the base is sodium or potassium hydroxide, sodium or potassium carbonate or bicarbonate, magnesium oxide, or a tertiary amine.

7. The method according to claim 6 wherein the tertiary amine is pyridine or triethylamine.

8. The method according to claim 1 wherein the reaction is carried out at a temperature between 0° C. and 30° C.

9. The method according to claim 1 wherein the pH is maintained at a constant value during said reaction.

10. The method according to claim 1 wherein the amino-carboxylic acid is natural or synthetic, optically active or inactive.

11. The method according to claim 6 wherein $R^1$ is tert-butyl, p-nitrobenzyl, 9-fluorenylmethyl, 2,2,2-trichloroethyl or trimethylsilylethyl.

12. The method according to claim 1 wherein said $R^3$ is substituted by an amino group and said amino group is protected by a benzyloxycarbonyl, t-butyloxycarbonyl, trichloroethyloxycarbonyl, 9-fluorenylmethyloxycarbonyl, vinyloxycarbonyl, acetyl, trifluoroacetyl, 2-bromobenzyloxycarbonyl or 2-chlorobenzyloxycarbonyl.

13. The method according to claim 1 wherein said $R^3$ is substituted by a COOH group and said COOH is protected by a benzyl, methyl or t-butyl group.

14. The process according to claim 1 wherein said $R^3$ contains an —NH or =NH group which is blocked by a tosyl, mesitylenesulfonyl, 4-methoxy-2,3,6trimethylbenzenesulfonyl, or benzyl group.

15. The process according to claim 1 wherein said $R^3$ is substituted by an OH group which is blocked by t-butyl, benzyl, methyl, acetyl, 2-bromobenzyloxycarbonyl, or 2-chlorobenzyloxycarbonyl.

16. The process according to claim 1 wherein said $R^3$ is substituted by an SH group which is protected by an acetamidomethyl, benzyl, diphenylmethyl, methoxymethyl, 4-methylbenzyl, trityl or a t-butyl group.

17. The method according to claim 1 wherein the aminocarboxylic acid is arginine in which the guanidino group is protected by a nitro group.

18. The method according to claim 1 wherein the amino acid is glycine, alanine, valine, leucine, isoleucine, phenylalanine, serine, threonine, lysine, δ-hydroxylysine, arginine, aspartic acid, asparagine, glutamic acid, sarcosine, glutamine, cysteine, cystine, methionine, tyrosine, phenylglycine, thyroxine, proline, hydroxyproline, tryptophan, histidine, nitroarginine, allo-isoleucine, allo-threonine, alpha-amino adipic acid, alpha-amino butyric acid, 7-amino heptanoic acid, gamma-amino butyric acid, epsilon-amino caproic acid, 3,4-dehydroproline, dehydroalanine, 3,5-dibromo tyrosine, 3,5-diiodo tyrosine, p-fluoro phenyl-alanine, p-iodo phenyl-alanine, p-bromo phenyl-alanine, homoproline, isoglutamine, isoserine, 1-amino cyclo-hexanoic acid, 6-amino penicillanic acid, thyronine, norleucine, norvaline, ornithine, statine, beta-alanine, gamma-methyl glutamic acid, gamma-tert-butyl glutamic acid, gamma-benzyl glutamic acid, 1-aminocyclopropanoic acid, azetidine 2-carboxylic acid, ethylglycinate, $N^{im}$-tosyl histidine, O-benzyl tyrosine, O-benzyl serine, O-benzyl threonine, epsilon benzyloxycarbonyl lysine, S-acetamidomethyl cysteine, tert-butyl glycine, beta-cyano-alanine, neopentyl-glycine, p-hydroxy-phenyl-glycine, delta-N-benzyloxycarbonyl ornithine, O-methyl serine, O-tert-butyl serine, O-methyl threonine, O-tert-butyl threonine, O-acetyl tyrosine, O-methyl tyrosine, O-2-bromobenzyloxycarbonyl tyrosine, O-2-chlorobenzyloxycarbonyl tyrosine, O-tert-butyl tyrosine, alanine methyl ester, N-methyl alanine, alpha-methyl alanine, $N^G$- (4-methoxy-2,3,6-trimethylbenzenesulfonyl) arginine, $N^G$ -tosyl arginine, $N^G$ -mesitylenesulfonyl arginine, beta-benzyl ester of aspartic acid, beta-tert-butyl ester of aspartic acid, beta-methyl ester of aspartic acid, gamma-carboxy-glutamic acid, gamma, $gamma^1$ -di tert butyl ester of carboxy glutamic acid, S-benzyl cysteine, S-diphenylmethyl cysteine, S-methoxybenzyl cysteine, S- (4-methylbenzyl) cysteine, S-trityl cysteine, S-tert-butyl cysteine, $N^{im}$- benzyl histidine, $N^{im}$ -mesitylenesulfonyl histidine, O-tert-butyl hydroxyproline, epsilon-acetyl lysine, epsilon BOC lysine, epsilon-trifluoroacetyl lysine, epsilon-2-bromobenzyloxycarbonyl lysine, epsilon-2-chlorobenzyloxycarbonyl lysine, said aminoacid being in the D,L or d,l form.

* * * * *